United States Patent [19]

Guenther et al.

[11] Patent Number: 4,831,645
[45] Date of Patent: May 16, 1989

[54] APPARATUS FOR POSITIONING THE HEAD OF A PATIENT FOR PRODUCING X-RAY PICTURES

[75] Inventors: Werner Guenther; Erich Heubeck; Manfred Muether, all of Bensheim, Fed. Rep. of Germany

[73] Assignee: Siemens Aktiengesellschaft, Berlin and Munich, Fed. Rep. of Germany

[21] Appl. No.: 100,221

[22] Filed: Sep. 23, 1987

[30] Foreign Application Priority Data

Sep. 26, 1986 [DE] Fed. Rep. of Germany ....... 3632878

[51] Int. Cl.⁴ .............................................. A61B 6/08
[52] U.S. Cl. ..................................... 378/205; 378/38; 378/99; 358/111
[58] Field of Search .................... 378/38, 99, 205–206; 358/111

[56] References Cited

U.S. PATENT DOCUMENTS

| | | | |
|---|---|---|---|
| 3,242,587 | 12/1980 | Lescrenier | 378/206 |
| 3,514,606 | 5/1970 | Rabey | 250/65 |
| 3,617,742 | 11/1971 | Schulman et al. | 250/61.5 |
| 3,708,663 | 1/1973 | Biederman | 378/206 |
| 4,117,337 | 9/1978 | Staats | 378/205 |
| 4,200,798 | 4/1980 | Neuesdorf et al. | 378/39 |
| 4,262,306 | 4/1981 | Renner | 358/111 |
| 4,409,616 | 10/1983 | Ledley | 358/111 |
| 4,600,949 | 7/1986 | Koizumi et al. | 358/229 |
| 4,694,478 | 9/1987 | Delnon | 378/38 |

FOREIGN PATENT DOCUMENTS 3436444 4/1986 Fed. Rep. of Germany .
7812569 11/1978 France .

OTHER PUBLICATIONS

Siemens sales brochure entitled, "Minimize X-Ray Dosage Maximize Image Quality . . . ".

Primary Examiner—Craig E. Church
Assistant Examiner—John C. Freeman

[57] ABSTRACT

An apparatus for positioning the head of a patient for producing dental panorama tomograms, which apparatus has an arrangement for positioning the head in a desired position relative to a fixed point with respect to at least one projection plane and this point, in turn, assumes a definite position relative to a central ray extending from the x-ray tube towards the x-ray picture, characterized by an arrangement for producing silhouettes and for projecting the silhouettes of the head in an actual position and in a desired position, simultaneously with the fixed point of each of the two silhouettes coinciding. By moving the head forming the silhouette of the actual position, the silhouette of the actual position can be moved to be congruent with the silhouette of the desired position to bring the head into the desired position for x-ray exposure.

15 Claims, 3 Drawing Sheets

APPARATUS FOR POSITIONING THE HEAD OF A PATIENT FOR PRODUCING X-RAY PICTURES

BACKGROUND OF THE INVENTION

The present invention is directed to an apparatus for positioning the head of a patient for producing an x-ray picture, particularly a dental panoramic tomogram, by means of which the head of the patient is positionable so that it assumes a defined position relative to a fixed point with respect to at least one projection plane and this fixed point, in turn, assumes a defined position relative to a central ray proceeding between an x-ray tube serving the purpose of producing an x-ray picture in an x-ray radiation receiver lying opposite to the x-ray tube.

A dental x-ray diagnostics installation comprising an x-ray source, an x-radiation receiver and means for positioning the head of a patient between the two is described in a Siemens Company sales brochure entitled "Minimize X-ray Dosage, Maximize Image Quality . . . ", Order No. A19100-M47-A361-01-766. The known apparatus comprises a light source, by means of which a stroke-shaped light marks are cast onto the head of a patient. These light marks comprise a defined position and define a course both relative to a fixed point, as well as relative to a projection plane belonging to the respective light mark. The head of the patient is positioned so that the stroke-shaped light marks coincide with pronounced lines at the head of the patient, for example, the Frankfurt Horizontals. The head of the patient then assumes the defined position relative to the fixed point required for the production of the picture and is held in this position by a head support. The positioning of the head of the patient with the known apparatus is an involved nature and is time-consuming. Moreover, the attending person must be present at the x-ray diagnostics installation during the step of positioning the head of the patient and they must then proceed behind the protective wall while producing or taking the x-ray picture.

In U.S. Pat. No. 3,708,663, whose disclosure is incorporated by reference, a similar positioning means is described for a cephalostat and the apparatus with which a skull picture of a patient can be produced. In order to be able to position the head of the patient in the three degrees of freedom (x, y, and z), a light beam projector, which generates both horizontal and vertical light rays, is provided. The light beam projector is arranged relative to the x-radiation source with the horizontal light ray and the central ray of the x-ray source lying in the same horizontal plane. A mirror, that reflects the vertical and horizontal light rays of the light beam projector, is positioned at a distance from the patient's head at an angle relative to the light rays of the projector and also at an angle relative to the vertical plane, which proceeds through the center of the patient's head. With the assistance of the reflected light rays and of the light rays directly cast onto the patient's head, the patient's head can be adjusted with respect to the Frankfurt Horizontal and with respect to the sagittal plane. Apart from the fact that the mirror being positioned immediately in front of the patient's head is disturbing, the alignment of the patient by visual comparison of the light rays directly cast onto the patient with the light rays reflected via the mirror, which are the indirect incident light rays, is comparatively involved and not precise.

U.S. Pat. No. 4,262,306, whose disclosure is incorporated by reference thereto, discloses an apparatus for supervision of the positioning of a patient or a region of a patient, which serves the purpose for repeat treatments of being able to bring the body or body part, respectively, of the patient into an optimally precise position, which coincides with the original position. To this end, a camera arranged spatially-rigid and/or source-rigid is provided. This camera is directed onto the patient and/or onto the radiation source. Picture elements of the first positional image are deposited in a storage by a camera. Comparison means are provided, first, with the picture element data of the first stored positional image and, secondly, with the second, current positional image produced during a repeated treatment and are subsequently converted so that the picture elements of both positions appear on an image carrier. On the basis of a correction of the position of the patient, the second and current positional image can be adapted and brought into coincidence with the previous image position. The storing of the first position can occur in a photographic way on the basis of an x-ray picture or on the basis of electromagnetic memories. The comparison means can comprise an inverter and an addition circuit or can also comprise a subtraction circuit, with which the individual picture elements can be directly compared to one another and can be represented superimposed on one another. However, this patent does not teach how the patient's head can be exactly positioned for a panoramic tomogram, namely, during the initial exposure. The positioning for the initial exposure in this known apparatus continues to occur "manually" based on the feeling of the operational personnel. It is only repeat pictures, which can be reproduceably produced in this known apparatus, in accordance with the position during the first exposure. However, if, during the initial exposure, the exact position was not obtained, then subsequent exposures will also be out of position. Since an exact positionig of a patient's head is indispensible, particularly when producing tomograms of the jaw region of the patient, a device which provides exact initial positions and subsequent positions is desired.

SUMMARY OF THE INVENTION

The object of the present invention is to achieve an improvement in an apparatus which has means for positioning a patient's head, which improvement enables an exact positioning of the head of the patient in a simple manner and with the least expenditure of time.

This is achieved by an improvement in a device or apparatus for positioning the head of a patient for producing x-ray pictures, particularly dental panoramic tomograms, which apparatus has means for positioning a head in a defined or desired position relative to a fixed first point with at least respect to one projection plane, said fixed first point, in turn, assuming a defined position relative to a central ray from an x-ray tube serving the purpose of producing an x-ray picture which is received by an x-radiation receiver lying opposite the x-ray tube. The improvements are means for registering a silhouette of the head of the patient and projection means for portraying the silhouette of the head of a patient in a plane proceeding parallel to the projection plane, said projection means including first means for portraying a silhouette of the head of the patient in an actual position relative to the fixed first point and second means for portraying a silhouette of the head of the patient in the desired position relative to the fixed first point, with each image being portrayed being projectible on top of one another so that the projection of the fixed first point and the central ray belonging to both silhouettes essentially coincide.

The objects of the invention are achieved because the projection means for portraying the silhouette of the head of the patient in a projection plane, which is either a plane parallel to the projection plane or the projection plane itself, are able to produce both a first silhouette of the head of the patient in the actual position, and a second silhouette of the head of the patient in the desired position relative to a fixed point, and these two silhouettes are superimposed, one on top of the other, so that the projection of the fixed point and central ray belonging to both silhouettes essentially coincide. In order to assure the exact positioning of the heat of the patient, which is required for producing the x-ray picture, the head of the patient, consequently, need only be aligned so that both silhouettes coincide. This can be accomplished quickly in a simple manner.

The means for recording the silhouettes of the head of the patient and the projection means for portraying the silhouette of the head of the patient can be constructed in many ways. Thus, the means for recording the silhouette can, for example, be formed by a photographic camera and the projection means can be formed by a projector. The photographic picture, for example, an instantaneous developed diapositive of the silhouette of the patient can be produced with the photographic camera for positioning the head of the patient and this, then, is projected onto a projection plane in a defined position with the projector so that the head of the patient is situated in the beam path. The head of the patient is then aligned so that the projection of the photographic exposure and then the shadow of the head cast onto the projection plane are congruent. However, it is also possible that the means for registering the silhouette are formed by an ultrasound transmitter and ultrasound sensor allocated thereto. The image of the head in the desired position and the actual image of the head in the actual position relative to a fixed point are then displayed. In this case, too, the head of the patient assumes its definite or desired position relative to the fixed point when the two silhouettes coincide in the viewing means. In another example, it is possible to fashion the means for registering the silhouette of the head of the patient as an infrared sensor and to portray the silhouette recorded with this on a suitable viewing means, again portraying the actual silhouette and the silhouette in the desired position relative to the fixed point. In this case as well, the exact positioning of the head of the patient is achieved when the two silhouettes coincide on the viewing means.

Both the positioning of the head of the patient, as well as the production of the x-ray picture, then proceeds in an especially simple way when a rest for the head of the patient, which assumes a definite position relative to the fixed first point, is provided. Particularly in conjunction with producing dental panoramic tomograms, it is advantageous when the rest is formed by a bite-down member for the front teeth of the patient and when the fixed point lies in the region of the bite-down member, which is intended to cooperate with the front teeth of the patient. Since the silhouette of the head of the patient is in its actual position relative to the fixed first point, it can be converted into the desired position relative to the fixed point by means of a simple rotation around this fixed first point.

It is provided in an expecially advantageous embodiment of the invention that the means for registering the silhouette of the head of the patient is formed by a video camera and the projection means for portraying the silhouette of the head of the patient is formed by a television monitor and that the system includes an image storage and an image processing means. The video camera, whose optical axis proceeds at right angles relative to the projection plane, will register the silhouette of the head of the patient and the monitor, simultaneously, displaces in the actual position relative to the fixed point and displays it in the desired position relative to the fixed point on the basis of the image storage and of the image processing means. The positioning of the head of the patient is, thus, accomplished so that the head of the patient is brought into a position that the two silhouettes displayed on the television monitor coincide. The image processing means is constructed so that it is in the position to modify the video signal representing the silhouette of the head of the patient in its actual position relative to the fixed point and so that the video signal which corresponds to the silhouette of the head of the patient in its desired position relative to the fixed point are generated by operations which correspond to displacement and/or rotation of the silhouettes of the head of the patient in the projection plane. So that this image processing procedure need be executed only once in conjunction with every positioning event, it is expedient to arrange the image processing means between the video camera and the image storage. The image storage then accepts the information corresponding to the silhouette of the head of the patient in its desired position relative to the fixed point so that this information is available for portrayal on the television monitor at any time, without having to reactuate the image processing means.

It is expedient, in view of the image processing and image storing when the video camera directly supplies a digital video signal. Then the image processing means can then be formed by a digital computer and the image storage can be formed by a digital memory. Since the high resolution of the standard video camera is not absolutely necessary in the present case, the video camera can be constructed as a CCD video camera.

In order to make an unambiguous statement available regarding whether the two silhouettes portrayed on the television monitor coincide, it is provided, in accordance with a modification of the invention, that the image processing means assigns a gray scale value or color value to the silhouette of the head of the patient in the desired position relative to a fixed point, which deviates from a gray scale or color value of a silhouette in its actual position relative thereto. The gray scale value or color value which results from those allocations to the silhouettes is then present in the regions in which the silhouettes coincide. As soon as the silhouettes completely coincide, only the resulting gray scale value or color value is then present.

In cases where the positioning of the head of the patient relative to the projection plane is inadequate, it can be provided that the video camera is optionally positionable so that its optical axis proceeds perpendicular to a second projection plane, which second plane defines an angle with first-mentioned plane. However, it is also possible to provide a second video camera, whose optical axis proceeds perpendicular to a second projection plane and the two planes describe the angle. When providing a second video camera, it can cooperate with the other video camera in such a manner and with the monitor with the image processing means and with the image storage that the portrayal of the silhouettes of the head of the patient optionally occur in one of the two projection planes. However, it can also be provided that a second video camera cooperates with a second monitor. In this case, the second video camera can have a second image processing means and second image storage allocated to it. It is, likewise, possible that a shared image processing means and a shared image storage, which are utilized in the multiplex process are provided for both video cameras and video monitors.

Other advantages and features of the invention will be readily apparent from the description of preferred embodiments, the drawings and claims.

DESCRIPTION OF THE PREFERRED EMBODIMENTS

Figure 1:
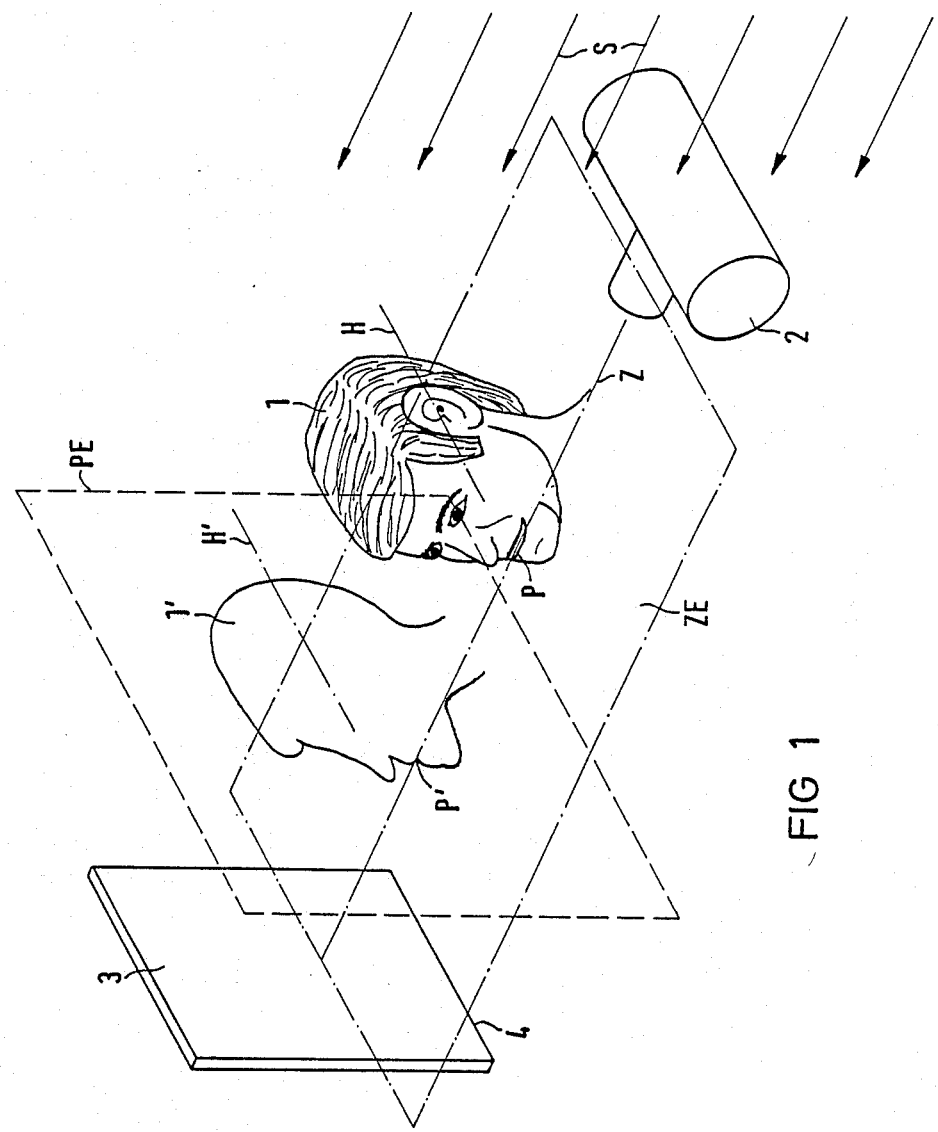
FIG. 1 is a schematic perspective view illustrating conditions on positioning the head of a patient relative to an x-ray unit.

The principles of the present invention are particularly useful for positioning the head 1 of a patient, which is arranged between an x-radiator or source of x-radiation 2 and an x-ray film cassette 3 for producing an x-ray picture, as illustrated in FIG. 1. The x-radiator 2 and the x-ray film cassette 3 can be components parts of a known x-ray diagnostics installation for producing dental panorama pictures, this installation is not shown in greater detail. In order to be able to produce the desired x-ray picture, the head 1 of the patient must assume a desired position relative to a fixed point P, with respect to a projection plane PE and this fixed point P, in turn, assumes a desired position relative to a central ray Z proceeding between the x-radiator 2 and the x-ray film cassette 3. Thus, a projection 1' of the head 1 of the patient obtained in the projection plane PE with the rays S, which, in the case of Fig. 1, proceed parallel, must assume a desired position relative to a projection P' of the fixed point P.

In the case of FIG. 1, the fixed point P lies on the central ray Z, which proceeds between the x-radiator 2 and the x-ray film cassette 3. The head 1 of the patient then assumes the desired position relative to the fixed or first point P with respect to the projection plane PE when it is positioned so that, first, the front teeth of the patient are situated in the region of the fixed point P and, secondly, when a Frankfurt Horizontal H, which is defined as a plane, when viewing the head 1 of the patient in profile, that proceeds from the lower edge of the eye socket and the outer auditory channel, proceeds parallel to a plane ZE, which contains the central ray Z and proceeds parallel to the edge 4 of the x-ray cassette. What this means, with respect to the projection plane PE, is that the projection of the front teeth of the patient coincide with the projection P' of the fixed point P and the projection H' of the Frankfurt Horizontal H must proceed parallel to the intersection of a straight line of the projection plane PE with the plane ZE.

Figure 2:
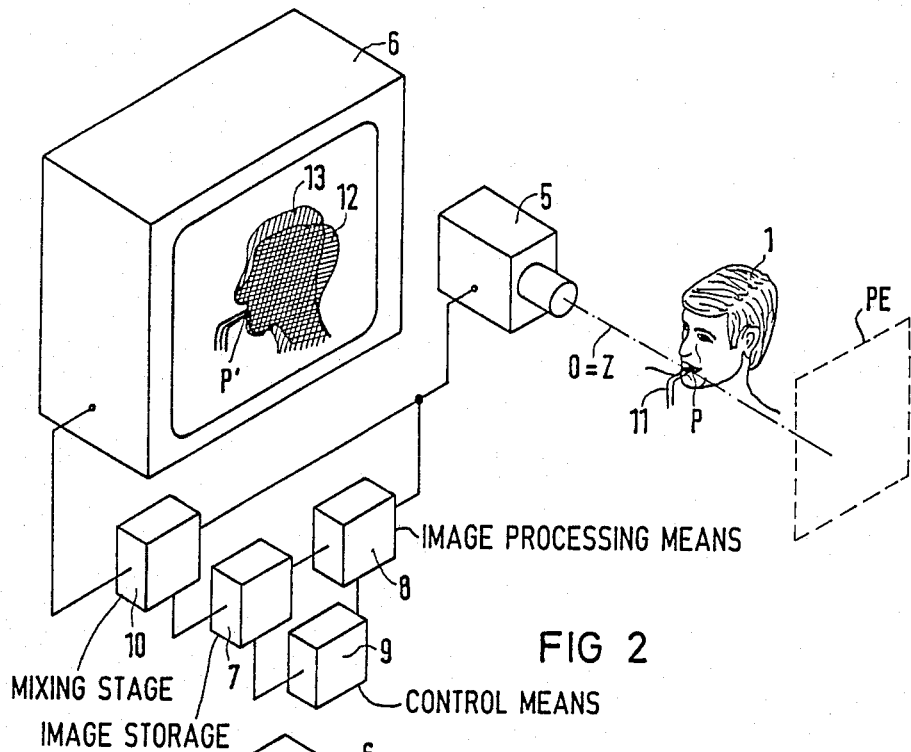
FIG. 2 is a schematic perspective view illustrating positioning a head in one plane.

In order to be able to position the head of the patient in the described way, the apparatus of the invention shown in FIG. 2 comprises means for registering the silhouette of the head 1 of the patient, and these means are formed by a video camera 5. The apparatus of the invention also has projection means for displaying the silhouette of the head 1 of the patient. The projection means is formed by a television monitor 6 in combination with an image storage 7, an image processing means 8 and a control means 9. A video signal produced by the video camera 5 will proceed to a mixing stage 10 directly and also, via said image processing means 8, and said image storage 7 and a resulting video signal is then supplied to the television monitor 6 from the mixing stage 10.

A rest formed by a bite-down member 11 is provided for supporting the head 1 of the patient. This bite-down member 11 is arranged so that the front teeth of the patient are situated in the region of the fixed first point P when the patient bites down on the bite-down member 11 with his front teeth.

The video camera 5 is adjusted so that its optical axis O proceeds through the fixed point P and strikes the projection plane PE at a right angle. When the video camera 5 is activated and the patient bites down on the bite-down member 11 with his front teeth, the silhouette 12 of the head of the patient consequently appears on the television monitor 6 in its actual position relative to the fixed point P' as a projection on the projection plane PE or, respectively, in a plane parallel thereto. In order to be able to bring the head 1 of the patient into a defined or desired position relative to the fixed point P with respect to the projection plane PE, the control means 9 initiates an image processing means 8 to transform the video signals supplied by the video camera 5 so that a video signal which corresponds to the silhouette of the head 1 of the patient in its desired position relative to the fixed point P occurs and comprises a gray scale value or color value deviating from the silhouette 12 of the head of the patient in its acutal position relative to the fixed point P. This video signal is transmitted into the image storage 7, from which it can be supplied to the mixing stage 10 by control means 9.

When this occurs, a silhouette 13 of the head of the patient in the desired position relative to the fixed point P appears on the television monitor 6 in addition to the silhouette 12 of the head 1 of the patient in the actual position relative to the fixed point P. The two silhouettes appear superimposed, one on top of the other, with the projection P' of the fixed points belonging to the two silhouettes 12 and 13 coinciding with each other. When deviating from FIG. 2, the fixed point P does not lie on the central ray Z proceeding between the x-radiator 2 and the x-ray film cassette 3,the condition that the projection of the central rays belonging to the two silhouettes 12 and 13 coincide must also be met in the display of the silhouettes 12 and 13 on the television monitor.

In order to bring the head 1 of the patient into its defined position relative to the fixed point P with respect to the projection plane PE, the head 1 of the patient must now be positioned so that the two silhouettes 12 and 13 are congruent. As indicated in FIG. 2 by different cross-hatching, this is facilitated in that the two silhouettes 12 and 13 comprise gray scale values or, respectively, color values, deviating from one another with the resulting gray scale value or color value being present in the region in which the silhouettes 12 and 13 overlap. The correct position of the head 1 of the patient is reached when only one silhouette is visible on the television monitor 6, with its gray scale value or, respectively, color value corresponding to the aforementioned resulting gray scale value or color value. Since the image processing means 8 is activated only at the beginning of every positioning procedure and the portrayal of the silhouette 13 of the head of the patient in the desired position relative to the fixed point after the initial start-up depends only on the image stored in the image storage 7, movements of the head of the patient undertaken during the positioning event have no influence on the silhouette 13 of the head 1 of the patient as the actual position is moved relative to the desired position.

Figure 3:
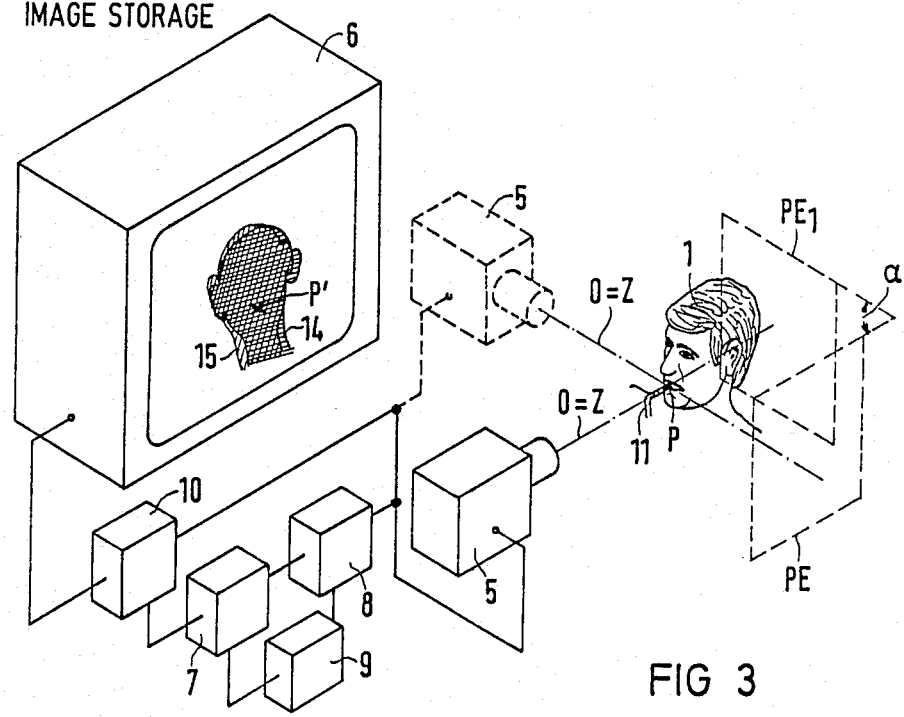
FIG. 3 is a schematic perspective view of the inventive apparatus for positioning the head in a second plane at an angle to the plane of FIG. 2.

The apparatus of the invention shown in FIG. 3 differs from that set forth above in that the video camera 5 is optionally positioned so that its optical axis O proceeds at right angles relative to a second projection plane $PE_1$, and the second projection plane $PE_1$ defines an angle $\alpha$ with the projection plane PE. It is then possible to position the head 1 of the patient, both with respect to the proection plane $PE_1$, positioning the head 1 of the patient relative to the fixed point P. FIG. 3 shows the two positions of the video camera 5, one of these being shown with broken lines, and this being selected such that the registration of the silhouettes of the head 1 of the patient occur in profile in one instance and occur frontally in the other. The two projection planes PE and $PE_1$ describe an angle $\alpha$ of about 90°. In the condition of the apparatus shown in FIG. 3, the positioning of the head of the patient occurs with respect to the projection plane $PE_1$. The silhouette 14 displayed on the television monitor corresponds to that of the head of the patient in its actual position relative to the fixed point P, whereas the silhouette 15 corresponds to that of the head in the desired position relative to the fixed point P.

Figure 4:
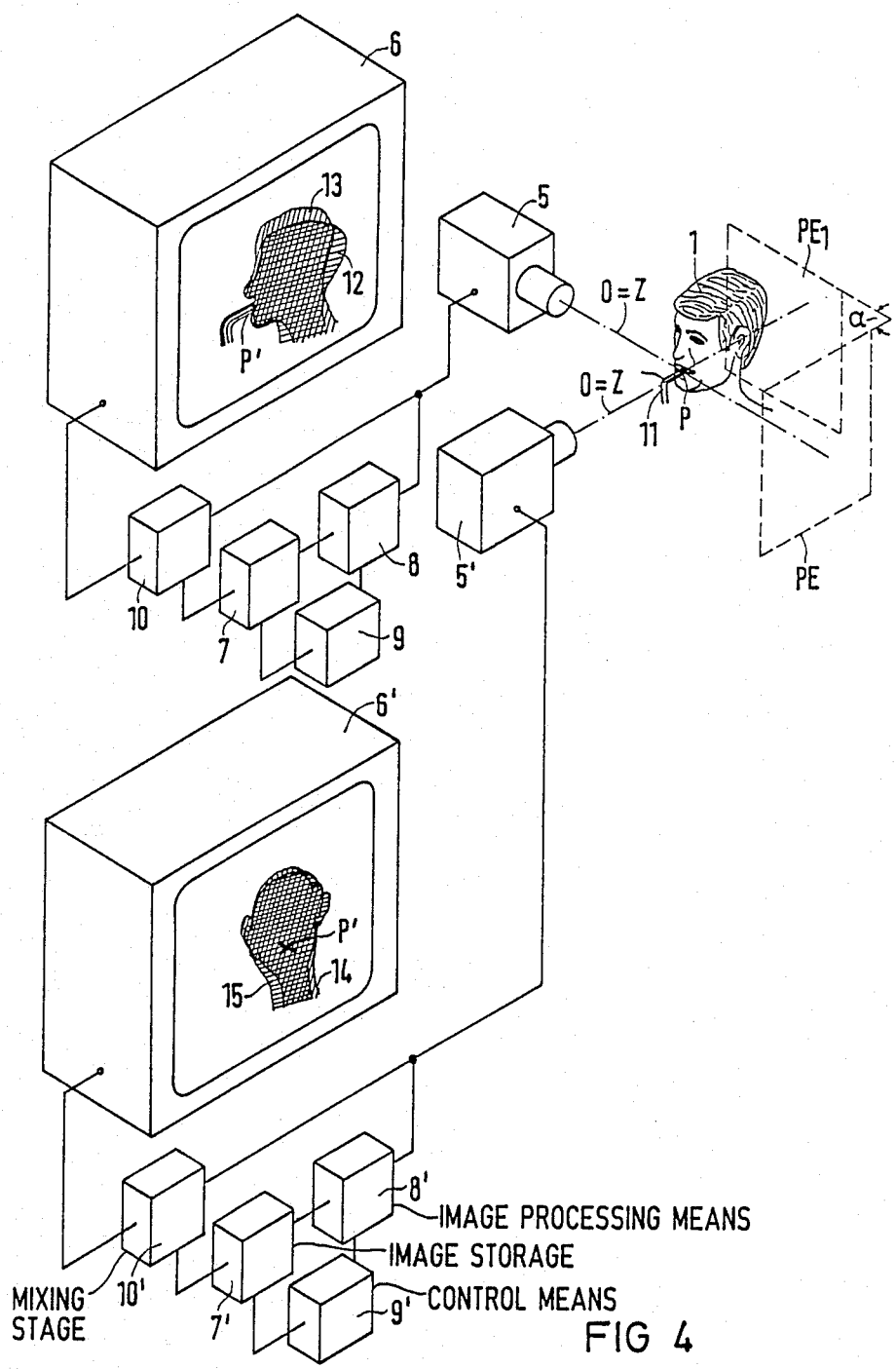
FIG. 4 is a schematic presentation of the inventive apparatus with an arrangement of positioning the heads in two planes simultaneously.

FIG. 4, likewise, shows an apparatus for the invention which allows the positioning the head of the patient with respect to two projection planes PE and $PE_1$. In this case, a video camera 5, 5' and a television monitor 6, 6', respectively, is provided for each of the two projection planes PE and $PE_1$. In addition, an image storage 7, 7', an image processing means 8, 8', a control means 9, 9' and a mixing stage 10, 10', respectively, are provided for each of the projection planes PE and $PE_1$, and these collaborating with the video cameras 5, 5' and with the television monitor 6, 6' in the above-described fashion so that the alignment of the head of the patient can occur simultaneous with respect to both projection planes PE and $PE_1$.

Regardless of the specific embodiments of the means for registration and of the projection means for the portrayal of the silhouette of the head of the patient, however, it is necessary that the projection of the silhouette of the head of the patient in its acutal and its desired position relative to the fixed point, respectively, occur in the same scale. This is because only with the same scale do the two projections of the fixed point and the central ray belonging to the two silhouettes coincide and only then can the two silhouettes be brought into coincidence.

Although various minor modifications may be suggested by those versed in the art, it should be understood that we wish to embody within the scope of the patent granted hereon all such modifications as reasonably and properly come within the scope of our contribution to the art.

We claim:

1. In an apparatus for positioning the head of a patient while producing an x-ray picture of a jaw of a patient including a dental panorama tomogram, said apparatus having a source of x-rays or projecting x-rays along a path having a central ray and said apparatus having means for receiving the x-rays, said apparatus further including means for positioning the head of the patient in a desired position relative to a fixed first point with respect to at least one projection plane, said fixed first point, in turn, assuming a definite position relative to the central ray of the source of x-rays, the improvements comprising said means for positioning the head of the patient having a bite-down member for the front teeth of the patient and said fixed first point lies in the region of the front teeth engaged on the bite-down member, means for registering silhouettes of the head of the patient whose front teeth are engaging said bite down member and projection means for portraying the silhouette of the patient in a plane parallel to the projection plane, said projection means having means to portray a first silhouette of the head of the patient in an actual position relative to the fixed first point and said projection means having means to create a second silhouette of the head of the patient in a desired position relative to the fixed first point from said first silhouette of the head of the patient in the actual position and said projection means having means to portray said first and second silhouettes simultaneously by superimposing said first and second silhouettes on top of one another so that the projection of the fixed first point and the central ray belonging to both of said first and second silhouettes essentially coincide.

2. In an apparatus for positioning the head of a patient while producing an x-ray picture of a jaw of a patient including a dental panorama tomogram, said apparatus having a source of x-rays for projecting x-rays along a path having a central ray and said apparatus having means for receiving the x-rays, said apparatus further including means for positioning the head of the patient in a desired position relative to a fixed first point with respect to at least one projection plane, said fixed first point, in turn, assuming a definite position relative to the central ray of the source of x-rays, the improvemets comprising said means for positioning the head of the patient having a bite-down member for the front teeth of the patient and said fixed first point lies in the region of the front teeth engaged on the bite-down member, means for registering silhouettes of the head of the patient whose front teeth are engaging said bite down member and projection means for portraying the silhouette of the patient in a plane parallel to the projection plane, said projection means having means to portray a first silhouette of the head of the patient in an actual position relative to the fixed first point and said projection means having means to create a second silhouette of the head of the patient in a desired position relative to the fixed first point with the portraying of said first and second silhouettes being superimposed on top of one another so that the projection of the fixed first point and the central ray belonging to both of said first and second silhouettes essentially coincide, said means for registering said first and second silhouettes of the head of the patient being formed by a video camera, said projection means for portraying said first and second silhouettes of the head being formed by a television monitor, and image storage and an image processing means, said video camera having an optical axis extending at right angles relative to the projection plane to register a first silhouette of the head of the patient, said image processing means and image storage creating a second silhouette of the desired position relative to the fixed first point from the first silhouette of the actual position, and said monitor simultaneously portraying the second silhouette with the first silhouette.

3. In an apparatus according to claim 2, wherein said image processing means is arranged between said video camera and said image storage.

4. In an apparatus according to claim 3, wherein said video camera directly supplies a digital video signal, said image processing means is formed by a digital computer and said image storage is formed by a digital memory.

5. In an apparatus according to claim 4, wherein said video camera is a CCD video camera.

6. In an apparatus according to claim 2, wherein said image processing means allocates a gray scale value or color value to the silhouette of the head of the patient in the desired position relative to the fixed first point, which desired position is derived from a silhouette of the actual position relative to said fixed point.

7. In an apparatus according to claim 2, wherein said video camera is optionally positionable so that said optical axis proceeds perpendicular to a second projection plane, said second projection plane forming an angle, with said first mentioned projection plane.

8. In an apparatus according to claim 2, wherein a second video camera is provided, said second video camera having an optical axis extending perpendicular to a second projection plane and said second projection plane forming an angle with said first mentioned projection plane.

9. In an apparatus for positioning the head of a patient while producing an x-ray picture of a jaw of a patient and including a dental panorama tomogram, said apparatus having a source of x-rays for projecting x-rays along a path having a central ray and said apparatus having means for receiving said x-rays, said apparatus further including means for positioning the head of the patient in a desired position relative to a fixed first point with respect to at least one projection plane, said fixed first point, in turn, assuming a definite position relative to the central ray of the x-ray tube, the improvements comprising means for registering first and second silhouettes of the head of the patient and projection means for portraying said first and second silhouettes of the patient in a plane parallel to the projection plane, said means for registering said first and second silhouettes of the head, comprises a video camera having an optical axis extending at right angles relative to the projection plane to register said first silhouette of the head of the patient, said projection means being capable of simultaneously portraying said first silhouette of the head of the patient in an actual position relative to the fixed first point and said second silhouette of the head of the patient in a desired position relative to the fixed first point with the portraying of said first and second silhouettes being superimposed on top of one another, said projection means including a television monitor, an image storage, and an image processing means, said image processing means creating said second silhouette of the desired position from said first silhouette of the actual position, and said television monitor simultaneously portraying said first silhouette of the actual position and said second silhouette of the desired position so that the projection of the fixed first point and the central ray belonging to both silhouettes essentially coincide.

10. In an apparatus according to claim 9, wherein said image processing means is arranged between said video camera and said image storage.

11. In an apparatus according to claim 10, wherein said video camera directly supplies a digital video signal and said image processing means is formed by a digital computer and said image storage is formed by a digital memory.

12. In an apparatus according to claim 11, wherein said video camera is a CCD video camera.

13. In an apparatus according to claim 9, wherein said image processing means allocates a gray scale or color value to said second silhouette of the head of the patient in its desired position relative to the fixed point, which deviates from a color value or gray scale value of said first silhouette of the actual position relative thereto.

14. In an apparatus according to claim 9, wherein said video camera is optionally positionable in a second position, with said video camera having an optical axis extending perpendicular to a second projection plane, said second projection plane extending at an angle relative to said first-mentioned projection plane.

15. In an apparatus according to claim 9, which includes a second video camera having an optical axis extending perpendicular to a second projection plane, said second projection plane forming an angle with said first-mentioned plane, said second video camera having a second monitor with a second iamge storage and image processing means so that the images of said second video camera can be displayed simultaneously on the second monitor with the images of said first-mentioned camera on said first monitor.

* * * * *